(12) United States Patent
Homman

(10) Patent No.: US 8,712,141 B2
(45) Date of Patent: *Apr. 29, 2014

(54) METHOD FOR COUNTING AND SEGMENTING VIRAL PARTICLES IN AN IMAGE

(75) Inventor: Mohammed Homman, Nacka (SE)

(73) Assignee: Intelligent Virus Imagaing Inc., Southern Pines, NC (US)

( * ) Notice: Subject to any disclaimer, the term of this patent is extended or adjusted under 35 U.S.C. 154(b) by 55 days.

This patent is subject to a terminal disclaimer.

(21) Appl. No.: 13/490,485

(22) Filed: Jun. 7, 2012

(65) Prior Publication Data

US 2012/0244524 A1   Sep. 27, 2012

Related U.S. Application Data

(63) Continuation-in-part of application No. 12/600,623, filed as application No. PCT/US2008/061499 on Apr. 25, 2008, now Pat. No. 8,224,059.

(60) Provisional application No. 60/940,870, filed on May 30, 2007.

(51) Int. Cl.
*G06K 9/00* (2006.01)
(52) U.S. Cl.
USPC ........................................................ 382/133

(58) Field of Classification Search
CPC ............ G06K 9/00127; G06K 9/0014; G06K 9/00147; G06T 7/0016; G06T 7/608; G06T 2207/10056; G06T 2207/30024; G06T 2207/30242
USPC ..................... 382/128, 133, 203, 225; 348/78
See application file for complete search history.

(56) References Cited

U.S. PATENT DOCUMENTS

| 6,888,139 B2 | 5/2005 | Tsuneta et al. ................ 250/311 |
| 7,034,299 B2 | 4/2006 | Nakagaki et al. .............. 250/311 |
| 8,224,059 B2 * | 7/2012 | Homman ........................ 382/133 |
| 2007/0099276 A1 | 5/2007 | Ott et al. ...................... 455/91.1 |

* cited by examiner

*Primary Examiner* — Andrew W Johns
(74) *Attorney, Agent, or Firm* — Fasth Law Offices; Rolf Fasth

(57) ABSTRACT

The method is for intracellular counting and segmentation of viral particles or infectious agents in an image. An image is provided that has a plurality of items therein. A radius range of viral particles is determined. Items in the image having a radius within the predetermined radius range are identified. Elliptical items that are formable from the predetermined radius range are determined. The round and elliptical items identified into groups are sorted. The viral particles among the round and elliptical items are identified. For example, the method may be used for intracellular counting and segmentation of siRNA treated human cytomegaloviral particles in TEM images.

6 Claims, 3 Drawing Sheets

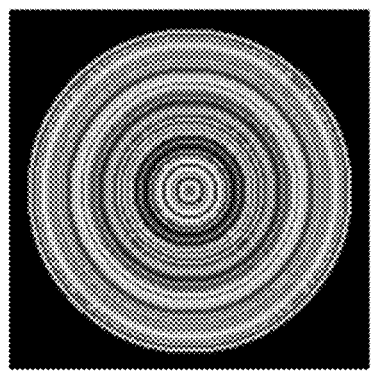
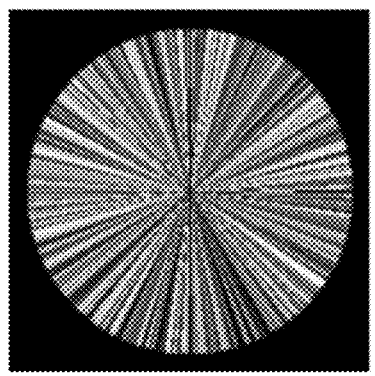
FIG. 1A  FIG. 1B
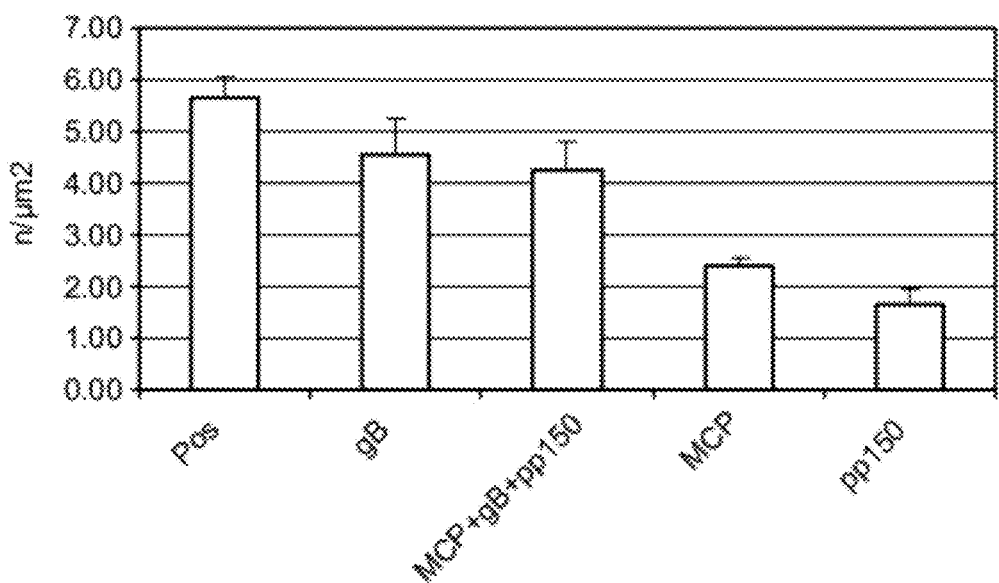
FIG. 2

METHOD FOR COUNTING AND SEGMENTING VIRAL PARTICLES IN AN IMAGE

PRIOR APPLICATIONS

This is a continuation-in-part application of U.S. patent application Ser. No. 12/600,623, filed 17 Nov. 2009 that claims priority from International PCT Application No. PCT/US2008/061499, filed 25 Apr. 2008 that claims priority from U.S. Provisional Patent Application No. 60/940,870, filed 30 May 2007.

TECHNICAL FIELD

The method relates to the counting, segmenting and identifying of objects such as viral particles depicted in an image such as electron microscopy images.

BACKGROUND OF INVENTION

Many efforts have been made in the past to classify and analyze cell structures that include viruses and other components. Various image analysis methods have been developed to describe, segment and classify viruses by using available image technologies. For example, cryo-electron microscopy has been used but the structures of the cells and the viral particles are not shown very well. It has also been difficult to objectively, repeatedly and reliably describe the cell components to accurately determine the maturity stages of the cell components.

More particularly, virus assembly is an intricate process and a subject of intensive research. Viruses utilize a host cell to produce their progeny viral particles by undergoing a complex process of maturation and intracellular transport. This process can be monitored at high magnification by utilizing electron microscopy (EM), which allows visual identification of different types of viral particles in different cellular compartments. Important issues that remain to be resolved include the identity of the viral proteins that are involved in each step of this virus assembly process as well as the mechanism of the underlying intracellular translocation and localization of different types of viral particles during virus maturation. Structural aspects of the virus maturation are generally hard to address although visualization techniques such as tomography and cryo EM have contributed to the available information on virus structures. These techniques may be used to provide information on stable mature viral particles. Genetic tools are available to produce mutants of key viral protein components. EM may be used to visualize the structural effects. However, there are no proper tools to characterize the structural effects, especially intermediate and obscure particle forms and to properly quantify them in an objective way.

This partly explains why the previous analysis methods have not been very effective and there is a need for more effective methods for analyzing cell and viral particle structures. There is a need for image analysis tools to characterize and quantify viral particle maturation and intracellular transport to facilitate objective studies of different virus assembly. There is also a need for an effective method for identifying and quantifying viral particles depicted in an image.

SUMMARY OF INVENTION

The method of the present invention provides a solution to the above-outlined problems. The method may be used for intracellular counting and segmentation of viral particles in images such as electron microscopy images. An image is provided that has a plurality of object/items therein. All round and elliptical objects in the image are identified. The round and elliptical objects are sorted into groups. A radial density profile of the round viral particles is determined. Elliptical items that are formable from the radial density profile of round viral particles are also determined. The viral particles are identified among the groups of sorted round and elliptical objects by analyzing radial density profiles of the objects in a selected group. For example, the method may be used for intracellular counting and segmentation of siRNA treated human cytomegaloviral particles in TEM images.

BRIEF DESCRIPTION OF DRAWINGS

FIG. 1A is a schematic example of a rotation invariant image (A);
FIG. 1B is a schematic example of an angular invariant image (B);
FIG. 2 is a graphical illustration of density measures for five sets of images.

DETAILED DESCRIPTION

The method of the present invention may be used for searching, segmenting and identifying particles/objects in images, such as objects depicted in transmission electron microscopy (TEM) images. The identified objects in the images may relate to viral particles and other particles such as infectious agent including bacterial that have round, elliptical and/or asymmetrical shapes and any other shape. Viral/virus particles and elliptical shapes have only been used as illustrative examples and the present invention is not limited to viral/virus particles and elliptical shapes. The current invention is not limited to virus and infectious agents, such as bacteria, but could also include proteins, antibodies, liposomes and other such substances. Also, the current invention is not limited to the exposure of infectious agents and proteins by pharmaceuticals, but could also include exposure by other chemicals, proteins and other such substances.

The elliptical shapes may be defined as having a maximum radius and a minimum radius while perfectly round shapes have one radius each. Preferably, the method determines which elliptical shaped, items can be formed from the radius range of the viral, particles to be analyzed. For example, if the viral particle has a radius of 100 units then the maximum radius and minimum radius of the elliptical shapes may, for example, be 20% greater (or 120 units) and 20% smaller (or 80 units) than the radius of the viral particle when the viral particle is round. If the maximum radius or the minimum radius is outside the allowable radius range then the item is considered unacceptable and will not be identified as a viral particle. The round and elliptical shapes are then sorted and grouped so that similar radial ranges are grouped together. Viral particles are then identified and quantified in the grouped shapes of items. It is also possible to identify viral particles that are between two different maturity stages i.e. that are in a maturity stage that is between two different maturity groups. The viral particles may have a predetermined radial density profile and a mathematical equation, such as Fourier transformation, may be used to determine which elliptical shaped objects, based on the predetermined radial density profile that is typical for the viral particles, are viral particles. Preferably, there is no need to use pamphlets that show radial density profiles of viral particles at certain maturity stages since damaged viral particles or viral particles that are between two different maturity stages of pamphlets may not be found by using the pamphlets.

Figure 3:
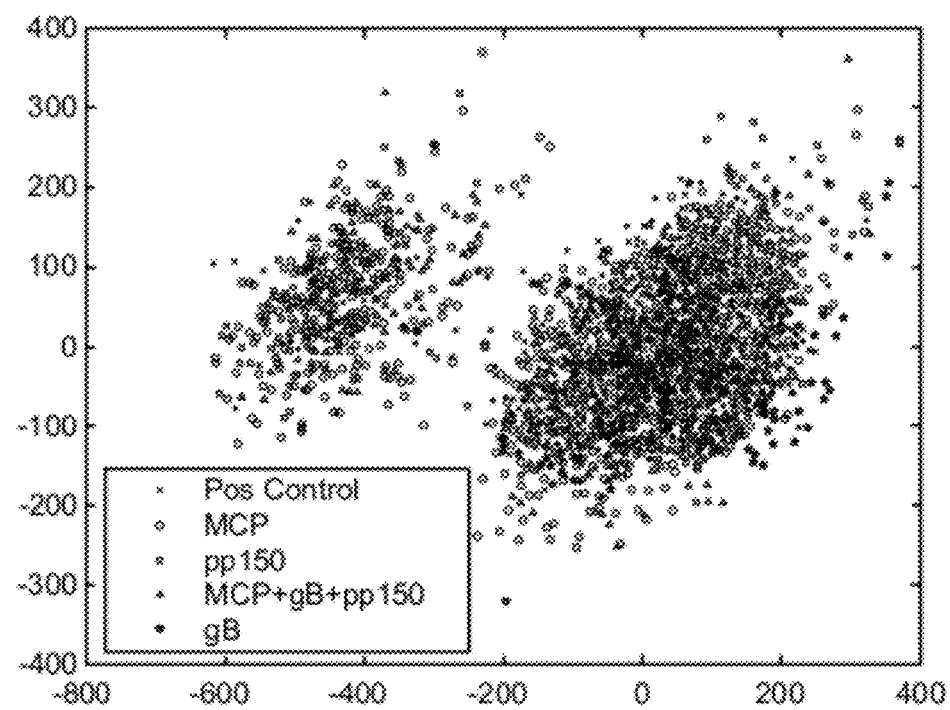
FIG. 3 is a schematic view of the radial density profiles from all sets of images placed in a LVS.

It may be possible to determine the distribution of radial ranges or radial density profiles in clusters, as shown in FIG. 3 and described in detail below. Also as described below, the viral particles may be exposed to a chemical substance, such as a pharmaceutical drug, and the method steps of the present invention may be run again based on the modified image to determine how the distribution of particles sizes or radial density profiles change as a result of the exposure to the chemical substance or medical treatment. In this way, it may be possible to determine the effectiveness of the chemical substance treatment on the viral particles.

It may also be possible to use siRNA techniques to block certain building blocks, such as by targeting pp150 proteins and blocking the production of cmv particle production, within the viral particles. After such siRNA treatments, the effect on the viral particles and the morphological/structural changes of the viral particles may be analyzed. Additionally, the number or quantity of viral particles affected may also be studied.

It may also be possible to use the method of the present invention to identify viral particles by analyzing the radial density profiles to decide which viral particles are depicted in an image. After finding all round and elliptical objects in an image and sorting the objects into groups based on radial characteristics, the next step may be to identify the radial characteristic of a particular viral particle. Any cluster of objects that have a radial characteristic within the predetermined radial range of the viral particle, such as within a radial range of 80+/−3 units, may thus be used to identify the viral particles. By using a range of radial characteristics deformed or elliptical particles may be included also. Particles with radial ranges outside this acceptable range are discarded and categorized as not being viral particles. If there are many types of viral particles within the desired radial range, it is possible to medically or chemically treat the viral particles and then run the method again to determine how the viral particles react to the treatment. Based on this reaction, it is possible to identify what the viral particle is. For example, it may be possible amplify DNA, such as by using PCR techniques, that creates a reference pamphlet that may be used to identify the viral particle. The additional test may thus be used to verify or confirm the viral particle identified.

The method of the present invention may thus be used for searching, segmenting and identifying viral particles in TEM images as described in detail below. Capsids of viral particles are approximately circular objects with the same protein density at fixed radii from the center, so called rotation invariant objects, as best shown in FIG. 1A. In order to create a measure of rotation invariance there is need for an "opposite" property to which the rotation invariance can be measured against. An angular invariant object may be used for this purpose since it has the same protein density at fix angles from the center as best, shown in FIG. 1B.

The Fourier spectrum of a function (f) which values are determined by the radius r, with corresponding Fourier frequency (wr), from the center and an angle (t), with corresponding Fourier frequency (wt), taken from any fixed direction out from the center may be used to illustrate a rotation invariant object and a angular invariant object. A perfect rotation invariant function has all its energy where wt=0, and a perfect angular invariant object has all its energy there wr=0 and all objects in between have energy in both frequency bands. A reasonably good measure is thus to compare the difference of these energies, giving an a priori measure with the threshold level of the measure as the only unknown constant, which can be given by a negative control.

A density measure of viral structures in TEM images is described below. A density measure to compare the number of viral structures in different images is introduced as a certain number of objects (n) per area unit A in an image.

$$d = \frac{n}{A}$$

Segmentation of different viral structures is described below. The radial density profile of each found object or item/particle serves as a good approximation of the viral structure. Setting the profiles in a linear vector space (LVS) with a basis set to the principal axes of the profiles, computed with a singular value decomposition (SVD), gives a visual understanding of cluster behavior of the different viral structures. With this information it is possible to extract different clusters and count individually, and discriminate structural differences when applying medical drugs by calculating the mean structure from each set of images.

Approximately 500 MB of images, as shown in Table 1 below, of infected cells with four different applied siRNA were acquired with electron microscope at a 3.3 nm/pixel resolution. The images were processed with the rotation invariance measure. The control radius of the rotation invariance was set to 15 pixels (about 50 nm) and objects in the images were acquired at local radial maxima of 15 pixels where the radial invariance measure exceeded a level of 15. When acquiring the radial density profiles the mean of each profile was removed in order to compensate for different brightness levels in the different images. The mean was taken over a radius of 100 pixels, about 330 nm.

TABLE 1

| Group | Number of images | Total area $\mu m^2$ |
|---|---|---|
| Positive control | 83 | 700.48 |
| MCP | 119 | 1317.30 |
| GB | 34 | 320.17 |
| MCP + gB + pp150 | 28 | 241.71 |
| pp150 | 28 | 355.84 |

Table 2 describes the mean and standard deviation of the mean of the calculated densities. Comparing the results from the pp150 and MCP images with the positive control with a student t-test gives p-values of $7.21*10-13$ and $2.19*10-11$ respectively to reject the hypothesis that the densities comes from distributions with equal mean.

TABLE 2

| Groups | Number of found objects (n) | Expected density n/μm² | Standard deviation of expected, density n/μm² |
|---|---|---|---|
| Pos | 3982 | 5.65 | 0.40 |
| GB | 2826 | 4.56 | 0.70 |
| MCP + gB + pp150 | 1343 | 4.24 | 0.54 |
| MCP | 1022 | 2.40 | 0.14 |
| pp150 | 652 | 1.66 | 0.28 |

FIG. 2 is a graphical illustration of density measures for five sets of images (Positive control, MCP, gB, MCP+gB+pp150 and pp150) with 1 standard deviation. MCP and pp150 exhibit significant smaller densities than the positive control.

Segmentation of viral structures is described below. The radial density profiles were plotted in a LVS, as best shown in FIG. 3, where the information from the two largest principal axis are shown. FIG. 3 shows the radial density profiles from all sets of images placed in a LVS. The image shows two well-separated clusters marked A and B that are described in more detail below. An important feature is that particles between two clusters are shown also. For example, those particles may be in maturity stages that are between the maturity stages represented by the clusters. It is often particularly important to study the particles in between clusters or groups of particles when the viral particles have been exposed to a pharmaceutical drug so that the effects of the drug may be determined.

Figure 4:
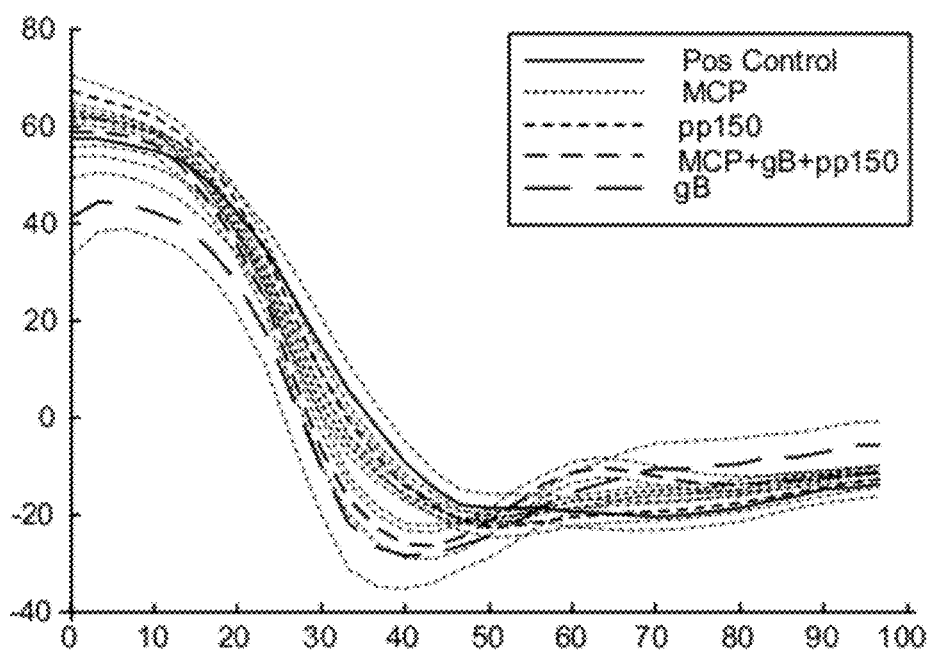
FIG. 4 is a schematic view of mean radial profiles with standard deviation in dash-dotted lines around the mean for subset A.

The mean radial density profiles for each set (positive control, MCP, pp150, gB and MCP+gB+pp150) for cluster A are shown in FIG. 4. This reveals the commonly known A (empty viral shells) classification of the HCMV maturation intermediates. Due to the fact that the number of objects found of this type is small, the objects have both small radial and angular energies, and the existence of many other non-viral structures in the set, no significant information can be extracted in addition to the information the capsid wall is situated at about 40 nm from the center.

Figure 5:
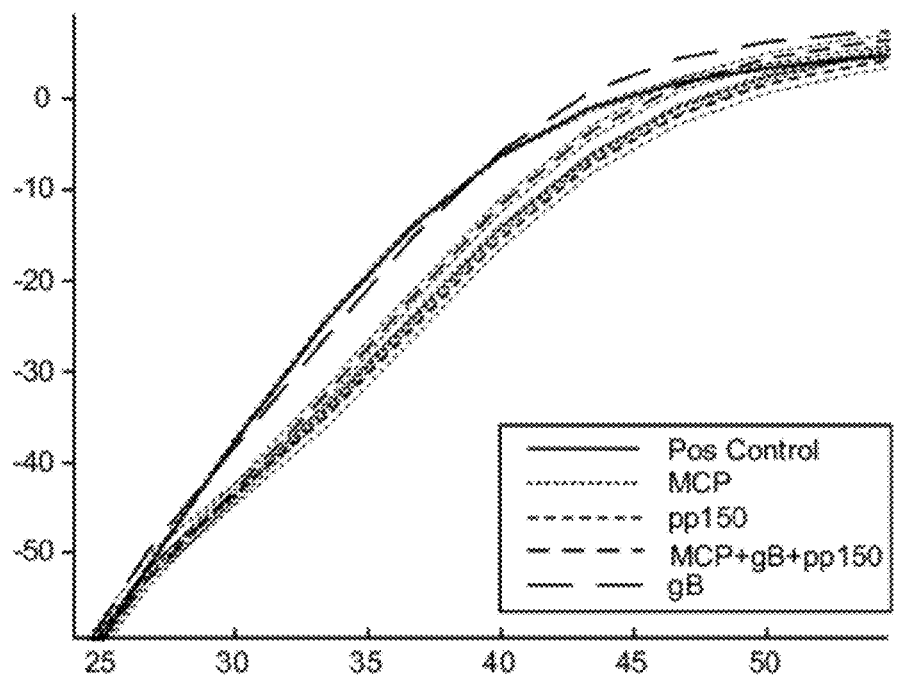
FIG. 5 is a schematic view of mean radial profiles with standard deviation in dash-dotted lines around the mean for the subset B.
Figure 6:
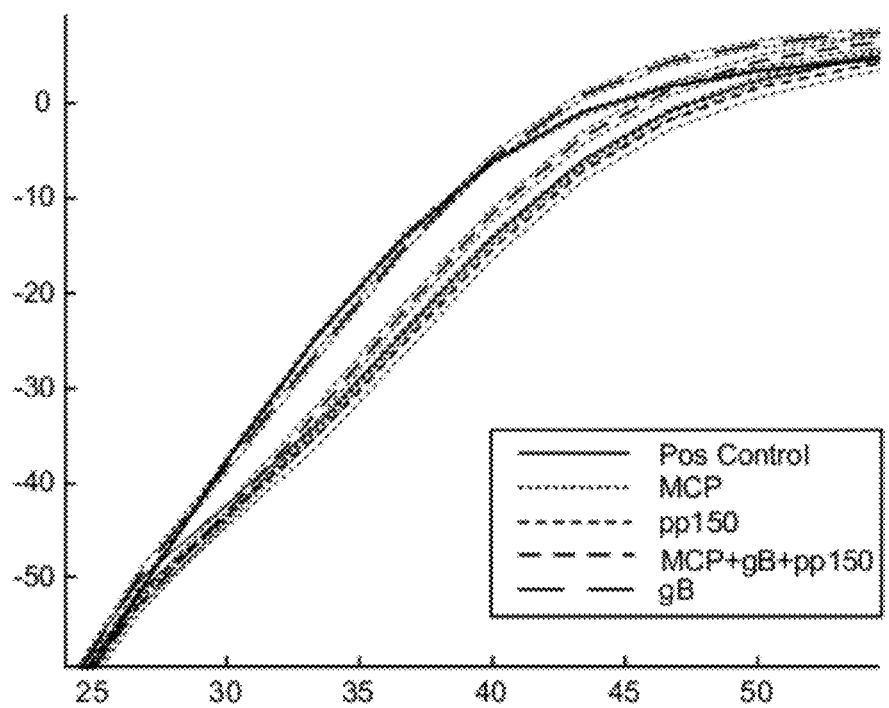
FIG. 6 is a schematic close up view of FIG. 5 at radii between 30 and 40 nm.

The mean radial density profiles for each set, (positive control, MCP, pp150, gB and MCP+gB+pp150) for cluster B are shown in FIG. 5. This reveals the commonly known B (capsids with translucent core) and C (mature capsids with dense core) classifications of the HCMV maturation intermediates. The positive control and gB sets differs from the MCP, pp150 and MCP+gB+pp150 sets at radii between 30 and 40 nm, as best shown in the close-up of FIG. 6, and in the center.

As a result, a model of viral particles in TEM images may be developed. The use of the angular invariant characteristic as a measure to compare with the rotation invariant characteristic can be exchanged by a fraction of the function energy that can be described by a rotation invariant object and the total energy. However, if the total energy is very small, the fraction may become numerically instable to compute.

To resolve this, a threshold level may be used. The use of a set threshold level is a source of subjectivity. However, at this level very few false structures were counted. A negative control group could though serve to set the threshold level and also to see the impact of the siRNA molecules.

Any orthonormal transformation of the density profiles, including the principal axes preserves the distance and inner product in the L2-LVS. Therefore, the clustering of different sub-structures is independent with respect of the choice of basis.

EXAMPLE

An example of materials and methods that may be used is described below. Human embryonic lung fibroblasts (HF) were maintained in bicarbonate-free minimal essential medium with Hank's salts (GIBCO BRL) supplemented with 25 mM HEPES [4-(2 hydroxyethyl)1-piperazine ethane-sulfonic acid], 10% heat inactivated fetal calf serum, L-glutamine (2 mM), penicillin (100 U/ml) and streptomycin (100 mg/ml) (GIBCO BRL, Grand Island, N.Y., USA). The cells were cultured, in 175 cm² tissue culture flasks (Corning, New York, USA) and used until passage 17. The cells were infected with HCMV at a multiplicity of infection (MOI) of 1. The virus supernatant was collected at 7 or 10 days post infection (pi). The virus supernatant was then cleared from cell debris by low speed centrifugation and frozen at −70° C. until used. Monolayers of HF cells grown in 96 well plates or on chamber slides were infected with HCMV AD169, at a multiplicity of infection (MOI) of 1.

Human pulmonary artery endothelial cells (HPAEC) were obtained from Clonetics, CA, USA. The cells were maintained in EBM-2 (Clonetics, CA, USA) with growth factors at 37° C. and 5% $CO_2$. One hour prior to infection, the medium was changed to EBM with 5% foetal calf serum and cultured in this medium during the infection process. The cells were cultured in 0.2% gelatine coated 175 cm² tissue culture flasks (Falcon) or 8 well chamber slides (Nalge Nunc International) and used until passage 8 in the experiments.

Human umbilical vein endothelial cells (HUVEC) were cultured in EGM medium (Clonetics, CA, USA). One hour prior to infection the medium was changed to EBM with 5% foetal calf serum and cultured in this medium during the infection process. The cells were cultured in 175 cm² tissue culture flasks (Falcon) and 8 well chamber slides (Nalge Nunc international) and used for experiments before passage 8. The cells were infected with at an MOI of 1 an endothelial adapted strain TB40.

Smooth muscle cells were isolated from aortic grafts obtained from patients undergoing surgery for aortic aneurysm with insertion of aortic grafts or from either aortic graft or graft of the iliaca vessels from transplantation donors. The cells were isolated by first removing the endothelial cells by cell scraping with a sharp instrument. The vessel was then divided into two different layers, the innermost layer (corresponding to the intima of the vessel) and the outermost layer (corresponding to the vessel media), by gentle separation of the two layers with a pair of tweezers. The aortic graft was cut into small 1 mm pieces and cultured on cell culture dishes in SMGM 2 medium (Clonetics) with the addition of SmGM-2 Single Quotes (hEGF 0.5 μg/ml, 0.5 ml; Insulin 5 mg/ml, 0.5 ml; hFGF-b 1 μg/ml, 1 ml; FBS 25 ml; GA-1000, 0.5 ml) for about 2 weeks, until there had been a SMC cell migration from the explants. The cells were cultured in 175 cm² cell-culture flasks (Falcon). To determine the purity of the SMC cultures, the cells were grown on chamber slides and fixed in 3% formaldehyde for 45 minutes at 4° C. and permeabilized with 0.3% Triton X for 5 minutes. After fixation the cells were stained for smooth muscle cell specific FITC conjugated anti-actin (SIGMA) and evaluated with fluorescence microscopy. The cells were fixed with methanol: aceton (1:1) at 4° C. for 5 minutes and stained with FITC conjugated anti-von Willebrand factor (Anti-vWF) and endothelial cell-specific von Willebrand factor and evaluated with fluorescence microscopy. Isotype controls for the antibodies were used in the experiments. The cultures were 100% positive for anti a-actin and negative for von Willebrand factor.

To examine virus infected cells by electron microscopy, uninfected and HCMV infected (MOI of 1) cells were harvested at 3, 5, 7 and 10 dpi, and fixed in 2% glutaraldehyde in 0.1M sodiumcacodylate buffer containing 0.1M sucrose and 3 mM $CaCl_2$, pH 7.4 at room temperature for 30 min. The cells were scraped of with a wooden stick and transferred to an Eppendorf-tube and further fixed over night in the refrigerator. After fixation cells were rinsed in 0.15 M. sodiumcacodylate buffer containing 3 mM $CaCl_2$, pH 7.4 and centrifuged. The pellets were then post-fixed in 2% osmium tetroxide in 0.07 M sodium-cacodylate buffer containing 1.5 mM $CaCl_2$, pH 7.4 at 4° C. for 2 hour, dehydrated in ethanol followed by acetone and embedded in LX-112 (Ladd, Burlington, Vt., USA). Sections were contrasted with uranyl acetate followed by lead citrate and examined in a Tecnai 10 transmission electron microscope (FEI, The Netherlands) at 80 kV. Digital images were captured by a Mega View IT digital camera (Soft Imaging System, GmbH, Münster, Germany).

The electron micrograph processing is described below. Sections were contrasted with uranyl acetate followed by lead citrate and examined in a Tecnai 10 transmission electron microscope (FEI, The Netherlands) at 80 kV. Digital images were captured by a Mega View II digital camera (Soft Imaging System GmbH, Münster, Germany) or electron micrographs were captured, developed and scanned for digitalization. The micrographs were digitized to 8-bit images in a HP ScanJet 6200C flatbed scanner to pixel sizes representing either 2×2 nm or 3×3 nm, giving capsid radii of approximately 25 or 17 pixels respectively, in the digitized micrographs. Each digital image has a size of approximately 1000× 1000 pixels (1 Mbyte). The resolution was satisfactory to distinguish between the three capsid classes investigated here, but the heavily textured background makes the capsid identification task very difficult. A DEC alpha personal workstation 433 running Hp Tru64 UNIX was used for development and evaluation of the method of the present invention. The implementation and testing was done using Matlab 7.0.1 (the MathWorks, Inc., Natick, Mass.). Generated gray level profile figures were processed in Corel Draw 10 (Corel Corporation, Ottawa, Canada) and Photoshop CS (Adobe Systems Inc, San Jose, Calif., USA).

While the present invention has been described in accordance with preferred compositions and embodiments, it is to be understood that certain substitutions and alterations may be made thereto without departing from the spirit and scope of the following claims.

The invention claimed is:

1. A method for analyzing infectious agents in an image, comprising:
   providing an image having a plurality of objects therein;
   identifying objects in the image;
   sorting the identified objects into groups;
   determining a radial density profile distribution of the identified objects;
   identifying asymmetrical objects that are formable from the radial density profile distribution;
   sorting the identified asymmetrical objects into groups; and
   identifying infectious agents among the sorted asymmetrical objects based on the radial density profile distribution of objects in a selected group of asymmetrical objects;
   exposing infectious agents to a pharmaceutical drug;
   sorting the infectious agents into groups after the exposure to the pharmaceutical drug; and
   analyzing a difference between the radial density profile distribution of infectious agents before the exposure with a radial density profile distribution of infectious agents after exposure to the pharmaceutical drug.

2. The method according to claim 1 wherein the method further comprises analyzing a change of distribution of sizes of the objects in the image as a result of the exposure.

3. The method according to claim 1 wherein the method further comprises determining difference in a quantity of objects in a group before and after exposure to the chemical substance.

4. The method according to claim 1 wherein the method further comprises analyzing morphological structures of viral particles.

5. The method according to claim 1 wherein the method further comprises counting and segmenting the infectious agents.

6. The method according to claim 1 wherein the method further comprises characterizing a morphology of the infectious agents.

* * * * *